US009669177B2

(12) United States Patent
Coleman (10) Patent No.: US 9,669,177 B2
(45) Date of Patent: Jun. 6, 2017

(54) VOICE RESPONSIVE FLUID DELIVERY, CONTROLLING AND MONITORING SYSTEM AND METHOD

(76) Inventor: Dennis R. Coleman, Allendale, NJ (US)

( * ) Notice: Subject to any disclaimer, the term of this patent is extended or adjusted under 35 U.S.C. 154(b) by 0 days.

(21) Appl. No.: 13/476,258

(22) Filed: May 21, 2012

(65) Prior Publication Data

US 2013/0275139 A1 Oct. 17, 2013

Related U.S. Application Data

(60) Provisional application No. 61/488,045, filed on May 19, 2011.

(51) Int. Cl.
| | | |
|---|---|---|
| A61M 16/06 | (2006.01) |
| G10L 15/00 | (2013.01) |
| A61M 16/00 | (2006.01) |
| A61M 16/10 | (2006.01) |
| A61M 16/20 | (2006.01) |

(52) U.S. Cl.
CPC .... *A61M 16/0677* (2014.02); *A61M 16/0672* (2014.02); *A61M 16/06* (2013.01); *A61M 16/0683* (2013.01); *A61M 16/101* (2014.02); *A61M 16/202* (2014.02); *A61M 2016/0033* (2013.01); *A61M 2205/3569* (2013.01); *A61M 2205/3592* (2013.01); *A61M 2205/581* (2013.01); *A61M 2205/80* (2013.01); *A61M 2209/088* (2013.01); *G10L 15/00* (2013.01)

(58) Field of Classification Search
CPC .............. A61M 16/00; A61M 16/0057; A61M 16/201; A61M 2205/3576; A61M 2205/3592

USPC .......... 128/200.24, 201.21, 203.12, 203.1, 4, 128/203.21, 203.23, 203.24, 203.29, 128/204.18; 222/5, 80–81, 83.5, 129, 222/131, 145.5, 183
See application file for complete search history.

(56) References Cited

U.S. PATENT DOCUMENTS

| | | | | |
|---|---|---|---|---|
| 4,342,725 A * | 8/1982 | Collins | .......................... | 422/126 |
| 4,559,941 A | 12/1985 | Timmons | | |
| 4,996,983 A | 3/1991 | Am Rhein | | |
| 5,193,534 A | 3/1993 | Peppler | | |
| 5,400,934 A | 3/1995 | Ducros | | |
| 5,582,164 A | 12/1996 | Sanders | | |
| 6,065,473 A | 5/2000 | McCombs | | |
| 6,526,968 B1 | 3/2003 | Izuchukwu | | |
| 6,595,207 B1 | 7/2003 | McDonald | | |
| 6,997,178 B1 | 2/2006 | Reynaud | | |
| 7,477,207 B2 * | 1/2009 | Estep | ................................ | 345/8 |

(Continued)

*Primary Examiner* — LaToya M Louis
(74) *Attorney, Agent, or Firm* — Katten Muchin Rosenman LLP (57) ABSTRACT

A system and methodology of delivery fluids and monitoring their status which is voice actuated. This system has application where a hands-free environment is preferred. Voice commands are given by the user via a Bluetooth® headset and received typically by the user's Smartphone. Voice recognition circuitry is programmed to recognize the simple commands and through complementing electronics, and electro-mechanical and mechanical elements, delivery at corresponding flow rates is accomplished. A further feature allows for respective voice commands to initiate a monitoring function where the status of any particular characteristic of the fluid can be relayed back to the user via the headset.

18 Claims, 8 Drawing Sheets

(56) References Cited

U.S. PATENT DOCUMENTS

| | | | |
|---|---|---|---|
| 7,753,049 B2* | 7/2010 | Jorczak et al. | 128/205.24 |
| 7,814,903 B2 | 10/2010 | Osborne | |
| 8,378,793 B1* | 2/2013 | Bryant | 340/384.1 |
| 8,869,793 B1* | 10/2014 | Spandorfer et al. | 128/203.14 |
| 2002/0166557 A1* | 11/2002 | Cooper | 128/206.28 |
| 2004/0206351 A1* | 10/2004 | McFarland, Jr. | 128/203.12 |
| 2004/0231667 A1 | 11/2004 | Horton | |
| 2005/0011520 A1* | 1/2005 | Rowe | A62B 25/00 |
| | | | 128/205.22 |
| 2005/0126571 A1* | 6/2005 | Jorczak et al. | 128/205.24 |
| 2007/0004969 A1* | 1/2007 | Kong et al. | 600/300 |
| 2007/0193585 A1 | 8/2007 | McDonald | |
| 2007/0197881 A1* | 8/2007 | Wolf et al. | 600/300 |
| 2008/0236584 A1* | 10/2008 | Holder | 128/204.23 |
| 2009/0000618 A1 | 1/2009 | Warren | |
| 2009/0175464 A1* | 7/2009 | Somen | A61B 17/00 |
| | | | 381/74 |
| 2009/0293875 A1* | 12/2009 | Kwok et al. | 128/204.18 |
| 2010/0024824 A1* | 2/2010 | Chalvignac | A61M 16/00 |
| | | | 128/205.24 |
| 2010/0263664 A1 | 10/2010 | Radivojevic | |
| 2010/0319689 A1 | 12/2010 | Kwok | |

* cited by examiner

VOICE RESPONSIVE FLUID DELIVERY, CONTROLLING AND MONITORING SYSTEM AND METHOD

CROSS-REFERENCE TO RELATED APPLICATIONS

This application claims the benefit of U.S. Provisional Application, Ser. No. 61/488,045, filed May 19, 2011, the entirety of which application is herein incorporated by reference.

FIELD OF THE INVENTION

The invention relates to a system and method for delivering oxygen and/or clean air or other fluids and more particularly to a hands and eyes-free, voice-activated system and method which minimizes or eliminates the interruption of the user's then, on-going activities.

BACKGROUND OF THE INVENTION

There are tens of thousands of skiers and snowboarders who go from near sea level to high elevation in the Rockies and Sierras to ski for a relatively short time. Therefore they must ski (snowboard) without having had the opportunity to acclimatize to the high elevation, which takes at least several days. This is also true in the case of mountain climbers, trekking devotees, mountain bicyclists and other high altitude enthusiasts.

Nowadays, if such a user wanted to obtain supplemental oxygen under these circumstances, he would typically have to stop his or her activity, access a hand-held canister of oxygen (which often would require the user to discontinue his activity, release his hands from his ski poles (or walking stick, bicycle, etc.)), and possibly take off his gloves in order to obtain the needed oxygen. This process by its very nature is often self-defeating, since the user needs the oxygen while he is expending energy and would prefer to continue his activity without frequent interruptions to "catch his breath".

Also, the 70 or so million Americans ("baby boomers") fast approaching retirement age, as a group, are known for their desire to maintain maximum functionality and mobility regardless of age. However, as individuals age, their maximum heart rate on average slows down on a linear basis— the maximum rate/minute on average is 220 minus the individual's age. Maximum heart rate is a good proxy for an individual's oxygen carrying capacity. As they continue to age, many of this cohort will need oxygen supplementation, optimally on a convenient hands-free and eyes-free basis in order to maintain their preferred activity level.

Also, many already are mobility compromised (e.g., those in so-called power chairs and scooters, those that are bedridden, blind, quadriplegic, or otherwise disabled). For them, to control and monitor the delivery of oxygen without having to divert their hands and eyes from controlling their mobility device would be ideal.

Furthermore, many in this group are already experiencing problems with arthritis. For those whose hands are arthritic, controlling the regulation of their medication delivery system by hand is a problem that this invention will solve.

Also, there are those on daily oxygen or other therapy regimens; and those who periodically work in dangerous atmospheric conditions (e.g., firemen). To enable them to control and monitor the status of their device on a hands-free and eyes free basis without having to interrupt their activities would be invaluable.

Various patents address systems that are designed to permit the wearer to breathe oxygen or purified air or administer other substances or medications. Consider the following:

Sanders, U.S. Pat. No. 5,582,164, discloses a portable gas delivery system that includes a gas storage assembly that is connected to a nose piece using flexible tubing. The gas storage assembly includes a strap that enables it to be readily carried by the person using this system.

AmRhein, U.S. Pat. No. 4,996,983, discusses a portable oxygen delivery system in which gas storage containers are incorporated into the temples on eyeglasses. Air delivery tubes extend around the wearer's ears to a nose plug that is placed in the wearer's nose.

Peppier, U.S. Pat. No. 5,193,534; and Timmons et al., U.S. Pat. No. 4,559,941, also describe incorporating an oxygen delivery system into eyeglasses. The oxygen is delivered from a storage container to the temples on the eyeglasses. The oxygen is then routed to a nosepiece through the eyeglasses.

Ducros, U.S. Pat. No. 5,400,934 describes a rucksack, or backpack, making it possible to drink, or inhale oxygen, while walking.

Izuchukwu, et al., U.S. Pat. No. 6,526,968, discusses an air delivery system that is incorporated into a utility belt that is worn by the user. The utility belt includes a pack for storing the compressed gas and a port for connecting to a mask using flexible tubing.

McDonald, et al., U.S. Pat. No. 6,595,207, describes an oxygen diffuser for a lightweight oxygen delivery system for a patient, the oxygen delivery system being of the type comprising a mount for seated engagement on a patient's head or ear, an elongated tubular boom for oxygen delivery secured at one end to the mount and having the diffuser secured to the other end, the diffuser to deliver oxygen passed through the boom to a space in the vicinity of the patient's nose and mouth.

McCombs, et. al., U.S. Pat. No. 6,065,473, describes a non-contact gas dispenser comprising a head set apparatus, a gas source and a conduit for directing the desired gas to a region proximate to the user's nose and mouth. The gas source preferably is a pressure swing adsorption apparatus that allows the user to select one of at least two predetermined settings of product gas, each setting having a distinct concentration and flow rate different from the other setting(s).

Warren, U.S. Patent Application No. US 2009/0000618, addresses a portable gas delivery system that includes a mouthpiece or nosepiece, a gas delivery pack and a medical cannula tubing assembly. It is adapted for use with a wireless transceiver for use with a cellular telephone or a personal music system and connected headphones.

Radivojevic, U.S. Patent Application No. US 2010/0263664 A1, addresses a portable oxygen delivery device and method for delivering oxygen to a mobile user. The device includes solar cells that harvest energy and instantaneously powers an electrolysis unit on user-demand for purpose of oxygen refreshment. The oxygen gas produced by the electrolysis unit is conveyed by tubing to an area in the vicinity of the user's mouth and nose. The solar cells and the electrolysis unit are integrated in a garment worn by the user. Note that although this device mentions the possibility (see paragraph 0081) of starting and stopping the electrolysis process in accordance with circumstances by the user, it does not imply in any way that a user controlled voice operated mechanism would be involved in this process or in the process of delivering the gas to the user. Note in this regard that the application states in the last two sentences of paragraph 0081 that, "in particular, the control can control the operation of the portable auction delivery device in accordance with receipt of a messages or a command string from a remote device or service. Such a service maybe located at a hospital, or maybe a server that monitors the data on air quality at the actual location of the mobile phone."

Horton, U.S. Patent Application No. US 2004/0231667 A1 relates to a medicament dispenser including a medicament container having a dispensing mechanism actuable by an actuator. The dispenser is particularly suitable for use as an inhalation device.

None of those listed, and others, including, Kwok (US 2010/0319689 A1, a sleep disorder related invention), and Osborne (U.S. Pat. No. 7,814,903) and Reynaud (U.S. Pat. No. 6,997,178) (each aircraft oxygen mask related inventions) however, incorporate a mechanism for controlling the delivery of the gas or other substance on a convenient voice activated basis (via a microphone or otherwise) or monitoring the status of the device on a hands-free and eyes-free basis by means of a voice activated response system using a headphone or other voice response mechanism directly to the user's ear.

It is therefore a primary object of this invention to provide an oxygen delivery system which responds to voice commands to begin and end the delivery of oxygen to a user.

It is a further object of the invention to provide such a system where certain properties of the delivery system, such as oxygen remaining, are communicated by detectable sensory signals including sounds representing widely known words.

It is a still further object of the invention to provide a hands-free and eyes-free, voice-activated oxygen delivery device, so as to permit the user to engage in his or her activity without necessarily stopping in order to catch his or her breath.

It is yet another object, to provide such a system which is convenient to carry and operate, hands-free and eyes-free, while in place on the person who is engaged in his or her activity.

SUMMARY OF THE INVENTION

Towards the accomplishment of these and many more objects and advantages, some of which will be readily apparent from the reading of the following, alone and together with the accompanying drawings, there is disclosed a voice responsive fluid delivery, controlling and monitoring system (and method) comprising a storage means having a quantity of fluid stored therein. In an anticipated preferred embodiment, this would be a gas such as air or oxygen. Means for releasing the fluid from the storage means interconnects with means for delivering the released fluid to the mouth and/or nose area of a user of said system.

The invention also includes means for monitoring at least a first property or characteristic of the stored fluid such as quantity remaining A first interconnect means is disposed between a voice responsive means and the means for releasing the fluid.

A second interconnect means is disposed between the voice responsive means and the means for monitoring the stored fluid.

The invention includes a third interconnect means disposed between the voice responsive means and the mouth area of an operator of the system whereby the transmission of voice commands from the operator to the voice responsive means is facilitated.

The voice responsive means device is adapted to respond to a first set of voice commands to produce a corresponding first set of electrical signals. This first set of electrical signals is supplied via the first interconnect means to the means for releasing the fluid. The latter is adapted to respond to respective ones of the first set of electrical signals in a corresponding respective way whereby the flow of fluid through the means for delivery is controlled.

The voice responsive means is further adapted to respond to a second set of voice commands to produce a corresponding second set of electrical signals. The second set of electrical signals is supplied via the second interconnect means to the means for monitoring the stored fluid. The monitoring means for monitoring the status of at least a first property or characteristic of the stored fluid is adapted to respond to respective ones of the second set of electrical signals in a corresponding respective way by generating a respective electrical signal of a third set of electrical signals evidencing the status of at least the first property sought to be monitored. The respective electrical signal of this third set of electrical signals that is prompted is communicated to the voice responsive means, which is still further adapted to generate, in the preferred embodiment, a respective sound for the respective one of the third set of electrical signals it receives.

A fourth interconnect means is disposed, in the preferred embodiment, between the ear area of the operator and the voice responsive means whereby the respective sound is transmitted to the ear area.

Preferably, the voice responsive means forms a part of a mobile phone such as today's Smartphone (for example, iPhone, android, blackberry, etc.).

Preferably, the voice responsive means is adapted to be programmed with a software application. This directs the voice responsive means to produce respective ones of the first set of electrical signals responsive to corresponding ones of the first set of voice commands The software application directs the voice responsive means to produce respective ones of the second set of electrical signals responsive to corresponding ones of the second set of voice commands The same or a second software application directs the voice responsive means to produce a respective sound, in the preferred embodiment, corresponding to a respective one of the third set of electrical signals.

Wireless technology such as Bluetooth® can be employed to implement the first, second, third and fourth interconnect means. However hard-wired technology can also be employed, alone or with the wireless technology, with more elaborate care taken to avoid entanglement in the various wires running about the body.

In the monitoring mode of the preferred embodiment, the voice responsive means produces a "respective sound" corresponding to the "respective one of the third set of electrical signals", to evidence the status of the property of the fluid sought to be monitored, for example, the volume of fluid remaining. Within the broader scope of the invention, as set forth in claim 1, a "further respective signal" is generated and transmitted to "an area in near proximity to sensory organ". The latter could be the user's eyes where the "further respective signal" presents itself as a visual display (perhaps on a watch-like device on the wrist); or as a vibration, again felt at the wrist, perhaps. The vibration could be pulsed a number of times or otherwise adapted so as to meaningfully relate the status of the characteristic sampled.

BRIEF DESCRIPTION OF THE DRAWINGS

A fuller understanding of the invention and its scope will be had from a reading of the following description especially when it is considered together with the accompanying drawings where.

DESCRIPTION OF THE PREFERRED EMBODIMENT

Figure 1:
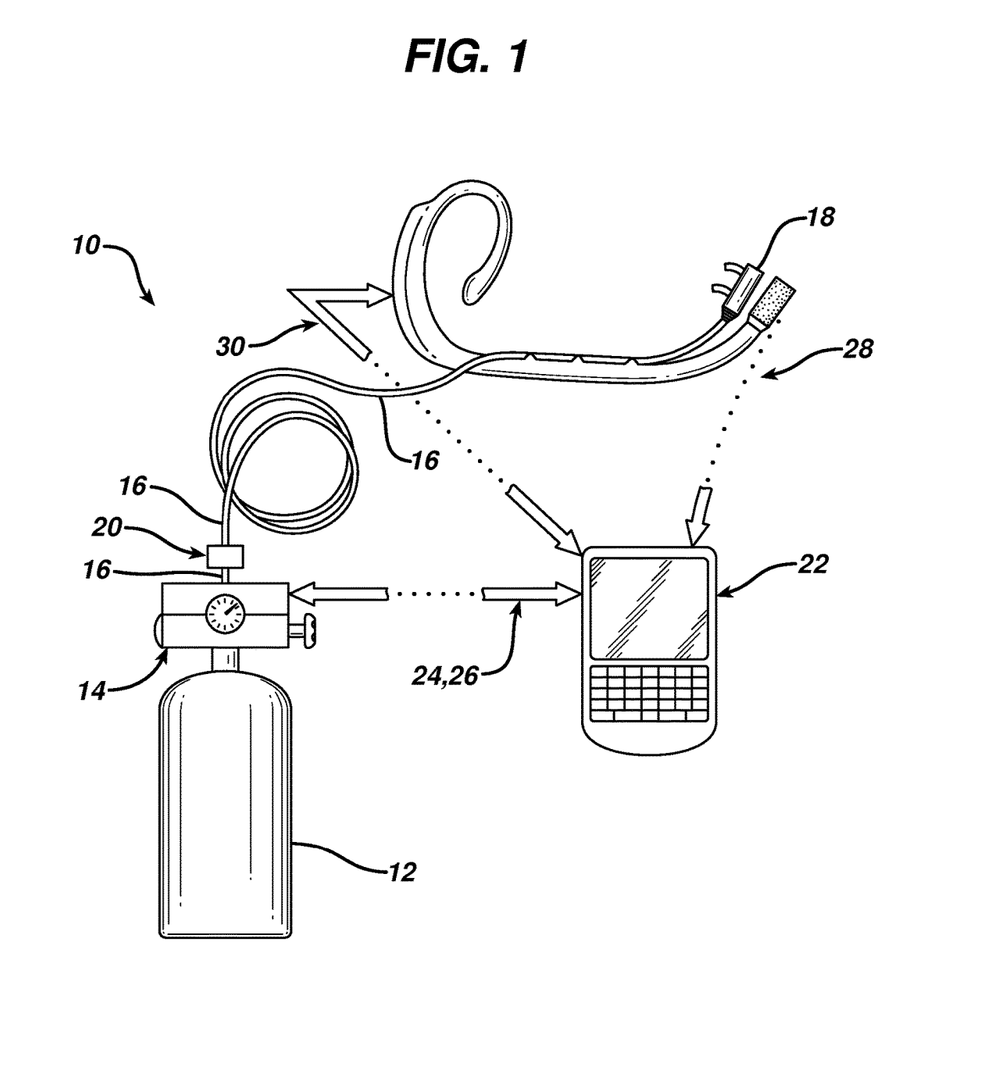
FIG. 1 is a schematic depiction of one embodiment of the invention.
Figure 2:
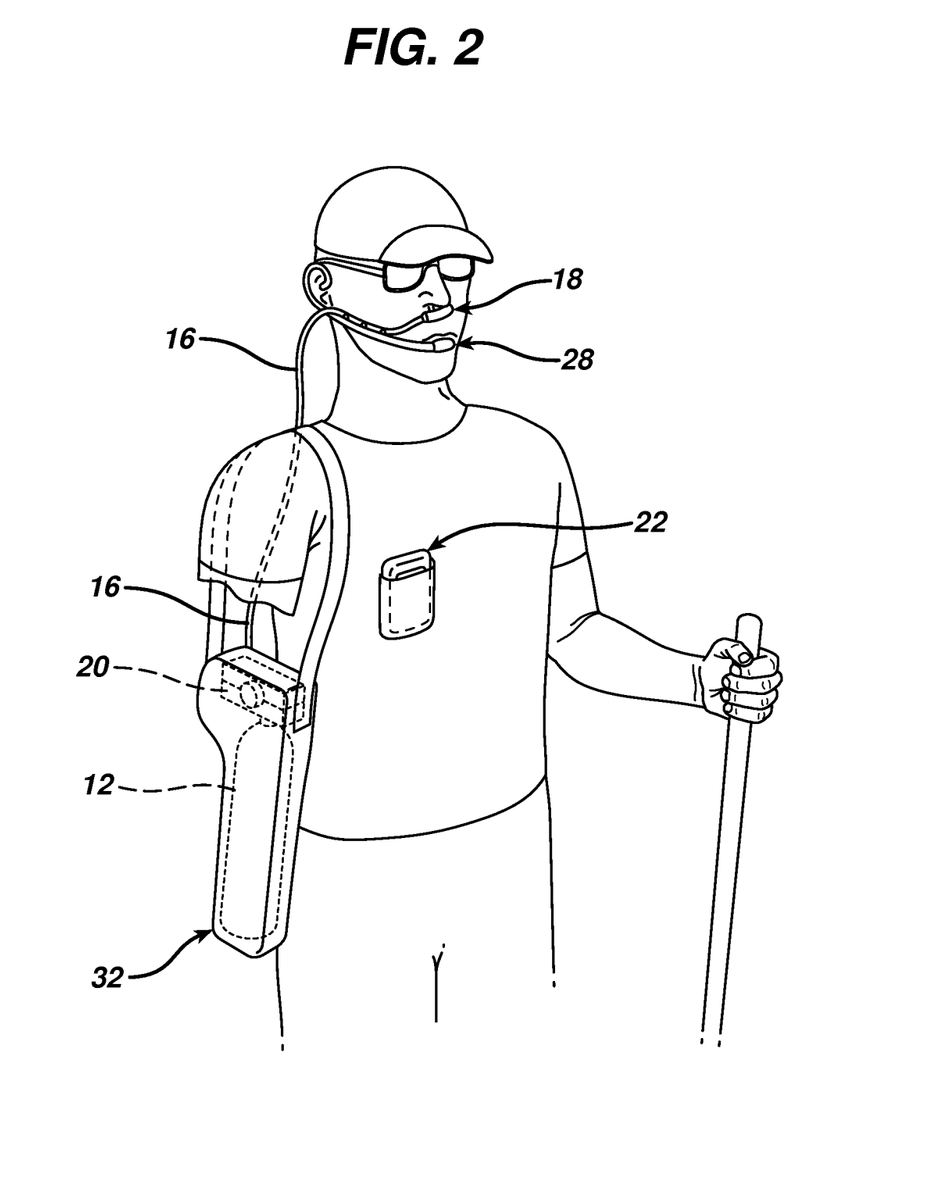
FIG. 2 is a perspective view of the embodiment of FIG. 1 in place on a user.

Referring now to FIG. 1, the elements of a voice responsive fluid delivery and monitoring system 10 are depicted in schematic form. In the basic variant, ideal for stressful and/or high altitude activities such as trekking, skiing, cycling, etc., there are several essential elements. The system 10 includes a storage means 12. This typically would be a supply of oxygen and includes any of the following:
  (a) an easily replaceable canister or canisters which would be carried by the user in a camelback style backpack, shoulder harness or holster (32 in FIG. 2);
  (b) a standard oxygen tank or cylinder which would be carried by the user on a camelback style backpack, shoulder harness or holster;
  (c) a portable oxygen concentrator (see, e.g., Radivojevic, Patent application #US 20100263664 A1 identified above) which would be carried by the user on a camelback style backpack, shoulder harness or holster, or
  (d) a similar gas source.

Means 14, including a valve assembly and associated electronics, is employed to release the fluid from the storage means 12. Flexible tubing 16, delivers the released oxygen from the storage means 12 to the mouth and/or nose area of a user of the system 10. The distal end of the tubing terminates in a nasal interface member 18 of known construction proximately disposed to the user's nose.

Means for monitoring 20 at least a first property, such as quantity remaining of the fluid (oxygen) stored in the storage means 12, is interposed in series in the path of tubing 16 between the valve assembly 14 and the nasal interface member 18.

Voice responsive means including a voice controlled device 22 provides the central control point for the system. In the preferred embodiment, the voice controlled device 22 is a Smartphone such as an iPhone or Android type. The voice control device 22 is programmed with an App that accepts simple voice commands to produce a uniquely corresponding first set of electrical signals. Alternately a voice recognition circuit can be placed on the electronic board 52 (see FIG. 3 and discussion below).

A first interconnect means or communication link 24 is disposed between the voice controlled device 22 and the means 14 for releasing the fluid from the storage canister(s).

A second interconnect means or communication link 26 is disposed between the voice control device and the means for monitoring 20 at least a first property of the stored fluid. Still further, a third interconnect means or communication link 28 is disposed between the voice controlled device 22 and the mouth area of the user of said system whereby the transmission of voice commands from the user to the voice controlled device 22 is accomplished. A fourth interconnect means or communication link 30 is disposed between the voice controlled device 22 and a sensory organ, or signal detection member of the user's body, here shown as the ear. (C)

The voice controlled device 22 is adapted through the use of appropriate voice recognition software, installed in the form of an App, to generate a first set of electrical signals based on a particular command word or words. For purposes of this invention, these include: START, POWER ON, AIR LOW, AIR MEDIUM, AIR MAX, STOP, and POWER OFF. To minimize battery power drain, the POWER ON and POWER OFF commands enable the circuitry powering the electromechanical device associated with the fluid releasing function described below. Besides this additional power requirement, the electronics are continually powered by the dc power source but the quiescent circuit current demand is sufficiently low as to not cause a concern about an excessive power drain. For the circuitry and electro-mechanical device employed, the system power requirements call for a 22 V DC supply with a current capacity of up to 1 Amp. The system would be powered by a rechargeable battery, replaceable battery and/or a solar battery.

After the voice recognition software is installed, the user pre-records these commands and those associated with the monitoring function, onto the voice recognition device via instructions provided with the App. A suitable software application for the iPhone Smartphone is available from Nuance Communications, Inc., located at 1 Wayside Road, Burlington, Mass. 01803.

The first set of electrical signals is communicated to the means for releasing the fluid 14 via wireless or hard-wire electrical connections. The voice controlled device 22 includes circuitry similar to the Bluetooth® headset which allows for transmission of digital data as well as vocal sounds, except, typically, its range is far greater than necessary in this application, since it routinely interfaces in a Wi-Fi environment.

The means for releasing the fluid 14 comprise related electronic circuitry; an electro-mechanical device to convert a respective electrical signal to predetermined mechanism movement, typically a specified aperture in the valve assembly 14; and a valve-stem engaging mechanical member responsive to the electro-mechanical device to enable the turning of the valve to a predetermined position based on the respective vocal command (AIR LOW, AIR MEDIUM or AIR MAX) from the user so as to release the fluid (oxygen) in the prescribed amount.

The user when he desires to check on the status, for example, the amount of the stored fluid remaining, utilizes a second set of voice commands to accomplish that. These include, for example, START, VOLUME, STOP. These voice commands are received by the voice controlled device 22 via the headset, and produce a corresponding second set of electrical signals. The signals are also supplied via the second interconnect means 26 to, in this case, the means for monitoring the characteristics of the stored fluid. One of the voice commands (VOLUME) would associate with one of the characteristics of the stored fluid that the user desires to check. This might be, for example, the quantity remaining of the fluid. Alternately, during the time the fluid (oxygen) is being delivered at the level requested, the user can vocalize the voice command necessary to initiate the status check, that is, VOLUME.

In response to that particular voice command, again for example purposes, the quantity of the remaining fluid, a corresponding third set of electrical signals for the determined status of that characteristic is generated by the means for monitoring 20. The corresponding electrical signals are communicated back to the voice controlled device 22 via the second interconnect means 26 which again might be a hard-wired or a wireless connection suitable for the transmission of digital electrical signals representative of the characteristic that is being checked.

The voice controlled device 22 containing a further software program or a modification of the first voice recognition software, then generates a respective sensory signal, corresponding to the received, respective third set of electrical signals and transmits that signal to the sensory member via a fourth interconnect means 30 disposed between the sensory member, again such as the user's ear, and the voice controlled device 22. This would be the standard Bluetooth® connection. To convert the data represented by the third set of electrical signals to a signal from which a sound can be generated, the voice controlled device 22, is programmed with software such as available from "Nextup Technologies, LLC" in Clemmons, N.C. Converting text to an audio representative signal on a Smartphone with Windows operating system is available from "Sayvoice Software Inc.", also known as "Sayvoice Company". Information as to this can be found at the "sayvoice.com" web site.

The received sensory signal is readily interpreted by the user as indicative of the status condition of the fluid property the user sought to monitor.

The voice controlled device 22 includes a voice user interface which enables it, when suitably pre-programmed, to convert the sounds it receives into respective electrical data. Voice controlled devices such as a Smartphone, have such voice recognition circuitry internal thereto since the messages received must be converted to a data format for transmission via a Wi-Fi network. It may be preferable however to utilize a relatively simple and straight forward voice recognition circuit for the purposes of the present invention only. This would be accessed through a corresponding App to be installed on the Smartphone, when it is desired to use a Smartphone as part of the overall system. The earlier mentioned App (available from Nuance Communications, Inc.) for the iPhone type Smartphone can be used or adapted for this purpose.

Figure 3:
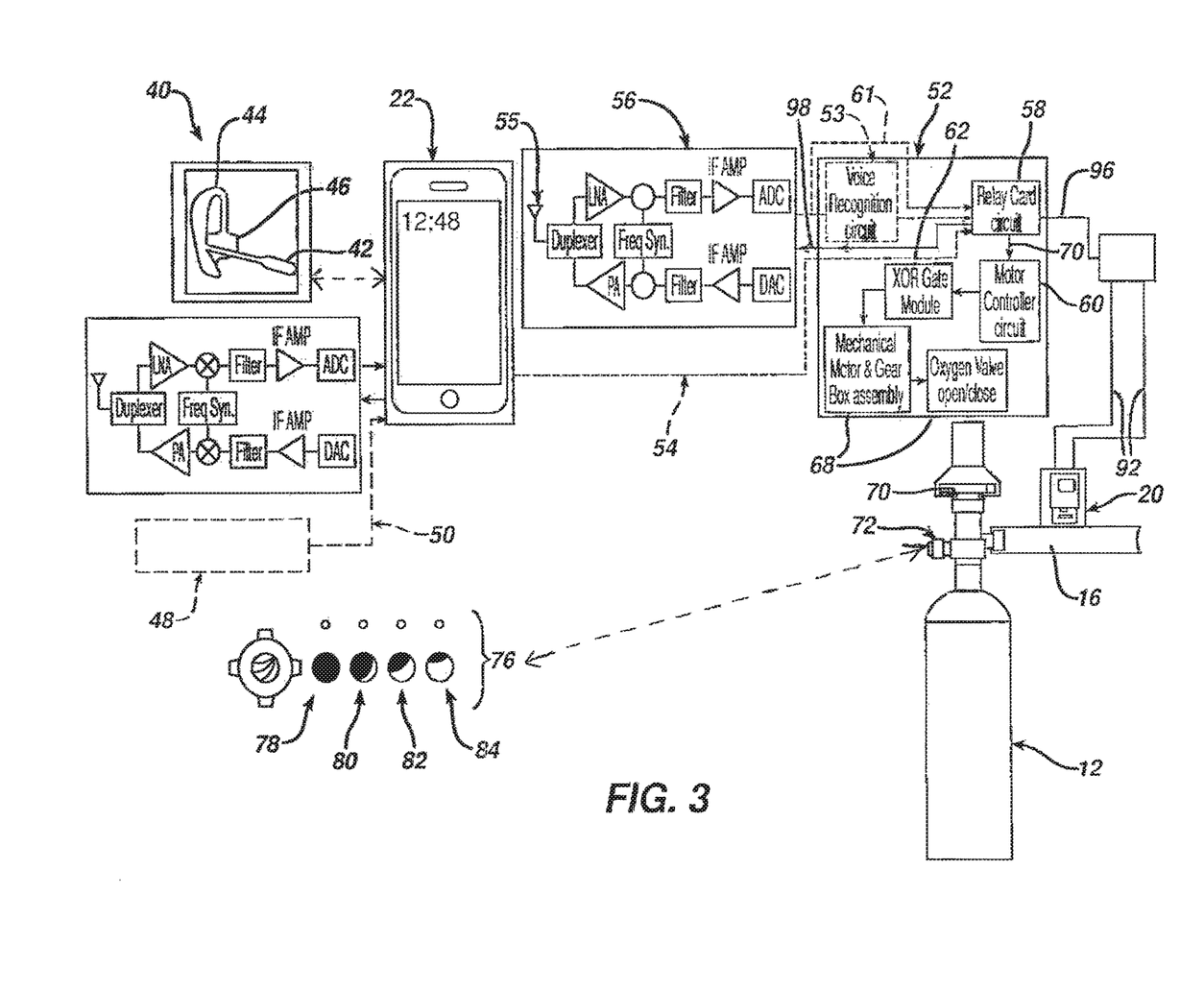
FIG. 3 is a detailed block diagram depicting the elements of one embodiment of the present invention.

Of course, if it is preferred to avoid modifying the Smartphone, the necessary circuitry similar, but again, simplified because of its limited function, can be employed on the separate electronics board 52. The circuitry again would be fashioned much like the circuitry in the Smartphone but due to its limited usage, presumably, it is much smaller in scale, capable of providing a communication link to and from the Smartphone; or, directly to a wireless or hard-wired headset, and able to receive data from the headset and the means for releasing and the means for monitoring portions of the present system. The design of such a speech to text system is set out in a paper located at the "Altera.com" web site.

Proceeding with the preferred embodiment that utilizes the Smartphone, the Smartphone would generate the respective first or second set of electrical signals and would transmit them to the electronic circuit board 52 typically positioned in close proximity to the fluid containing devices.

FIG. 3 depicts in block form, the various elements of such a system. These include the headset 40 shown as a so-called Bluetooth® headset which includes a microphone 42, a head-band 44 and an ear-piece 46. As noted above, a standard headset 48 shown in phantom can be hard-wired via connecting link 50 to the Smartphone in a known way. The voice controlled device 22, again, can transmit data to an electronic circuit board 52 either via a wireless interconnection or once again by way of hard-wire connection 54, shown in phantom. If by wireless interconnection, the transmitted data is received at antenna 55 of transceiver 56. The transceiver is of known construction and would be similar to that employed in the Smartphone device 22. "LS Research LLC" of Cedarburg, Wis., markets their Bluetooth® compatible TiWi transceiver module. Relevant information is available at their website.

The software App that would be employed with the Smartphone, in addition to generating the electrical data corresponding to a particular voice command received from the headset, would include an appropriately timed gating or enabling signal which would allow for wireless transmission of the electrical and data packet corresponding to a particular voice command (using the wireless transceiver of the device 22) to a wireless transceiver block 56 which is positioned on the circuit board 52 (but shown separately for clarity); or, via the hardwire connection to the input of the appropriate relay on relay card 58.

Electronic circuit block 52 in addition to the transceiver block 56, includes, as noted above, a relay card 58, a stepper motor controller circuit 60, and an exclusive or (XOR) gate module 62.

Figure 4:
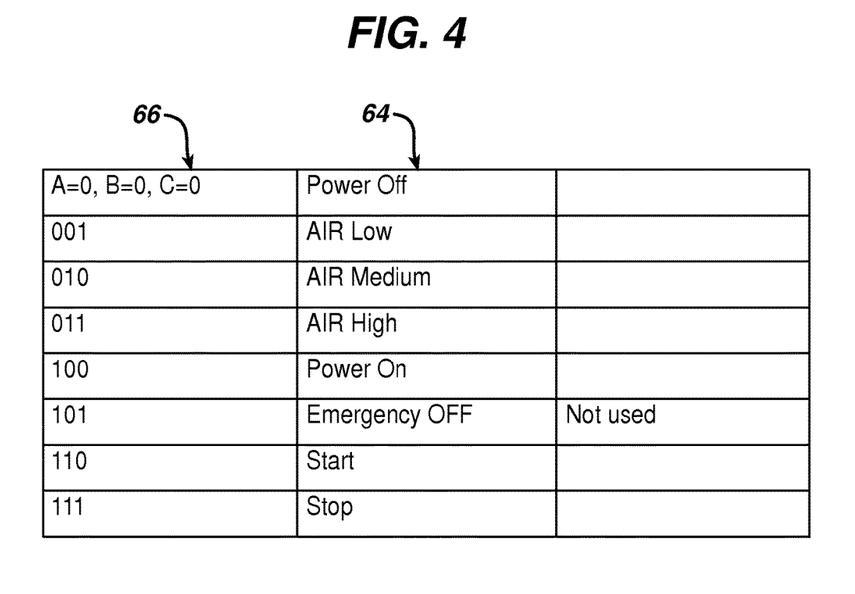
FIG. 4 depicts in table form a simple three bit logic scheme employed in the present invention.

For purposes of illustration, FIG. 4 sets forth in table form a three bit logic scheme providing three outputs, A, B and C. For purposes of this discussion, the various commands indicated in column 64 correspond to equivalent logic expressions as set forth in column 66. So for example, Power Off is represented by the three bit logic form 000; Power On by the logic expression 100. This table can be expanded to a 4 bit logic format for additional commands related to the fluid release function if required.

Relay card 58 includes a plurality of relays (electromechanical or solid state) as required to route received signals to the circuitry on the control board 52 as the circumstance dictates; and the means for monitoring 20. In the mode being presently discussed, the oxygen delivery mode, an appropriate scenario is as follows. The user, who is out of breath, decides he needs oxygen. By saying POWER ON the Bluetooth® head-set and system will be activated. The user would next say, perhaps, AIR LOW. When the command is recognized and transmitted to the transceiver 56 on the circuit board 52, the corresponding relay on the relay board is enabled via link 61. The received data for that command is then routed to the motor controller circuit input 70.

The motor controller circuit 60 receives the data signal and processes it and raises its power level to a point sufficient to drive the stepper motor to be discussed hereinafter. A suitable stepper motor controller IC is available from "Texas Instruments Incorporated". It is marketed under their product identifier, "DRV8811". Sufficient technical documentation on its power requirements and hook-ups can be found at Texas Instruments' web site.

This stepper motor controller circuit again processes the received signal. It includes two H-Bridge drivers as well as micro-stepping index logic to control a stepper motor's movement. The motor controller circuit device 60 can be configured to allow for an eighth step, quarter step and half step incremental movements.

Figure 5:
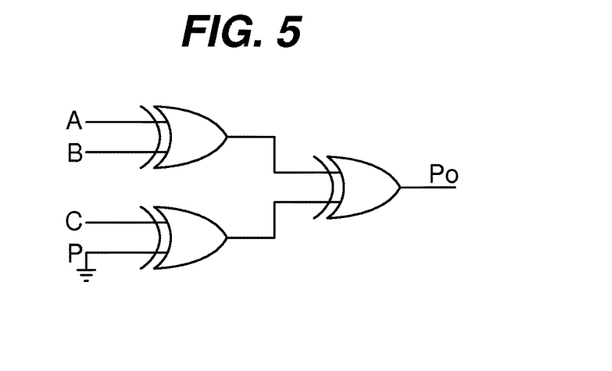
FIG. 5 is a logic drawing of an even-parity generator-checker circuit.

The powered-up signal is then processed by the exclusive logic block 62. This circuit acts as a parity generator/checker circuit. The purpose of this circuit is to insure the received signal maintains its integrity and corresponds in fact to the voice command now being implemented. The logic diagram for the even-parity checker is shown in FIG. 5. Inputs labeled A, B and C represent the three logic inputs depicted in the table of FIG. 4. If the P input is connected to logic "0", the logic circuitry of FIG. 5 will also allow the circuit to implement the parity generator. Output C represents the parity checker error signal.

When there is an error signal at output C the signal flow to the stepper motor contained within the "mechanical motor and gear box assembly" functional block 68 is interrupted. The user sensing the failure of the system in that no oxygen is received, again vocalizes the START command which will result in a reset signal to the XOR circuit 62. The AIR LOW command (in this illustration) will again be vocalized. Assuming the error is not enduring, the electrical signal will now reach the windings of the stepper motor portion of the motor and gear box assembly 68.

The "mechanical motor and gear box assembly" function 68 albeit not expressly depicted in the drawings, includes a stepper motor and appropriate gear assembly, as necessary. The latter couples the shaft of the stepper motor to the valve cap 70 of an air regulator valve 72 positioned on the top of the oxygen containing canister 12. The gearing assembly makes the appropriate adjustments to the movement of the stepper motor shaft to effect rotational movement of the air regulator shaft necessary to accomplish the oxygen valve openings, corresponding to STOP, AIR LOW, AIR MEDIUM and AIR HIGH vocal commands The corresponding oxygen valve openings are depicted in area 76 of FIG. 3 as 78, 80, 82, and 84 respectively.

The stepper motor converts the digital pulses from the stepper motor controller into mechanical shaft rotation. It is used in both industrial and commercial applications because of its low cost, high reliability and high torque at low speeds. The construction is simple but rugged and these devices operate in almost any environment. A stepper motor adaptable for the present invention is available from "Applied Motion Products", of Watsonville, Calif.

The valve regulator 72 together with a light-weight aluminum canister is available from "LIFE CORPORATION" of Milwaukee, Wis. These regulators maintain a precision flow rate from a full capacity cylinder to empty. Fixed flow rates at various liters per minute, such as 8, 16 and 24, corresponding to the AIR LOW, AIR MEDIUM and AIR HIGH positions, are available. The regulator affords a multi-position capability, if alternative, or more flow settings are desirable.

Figure 6:
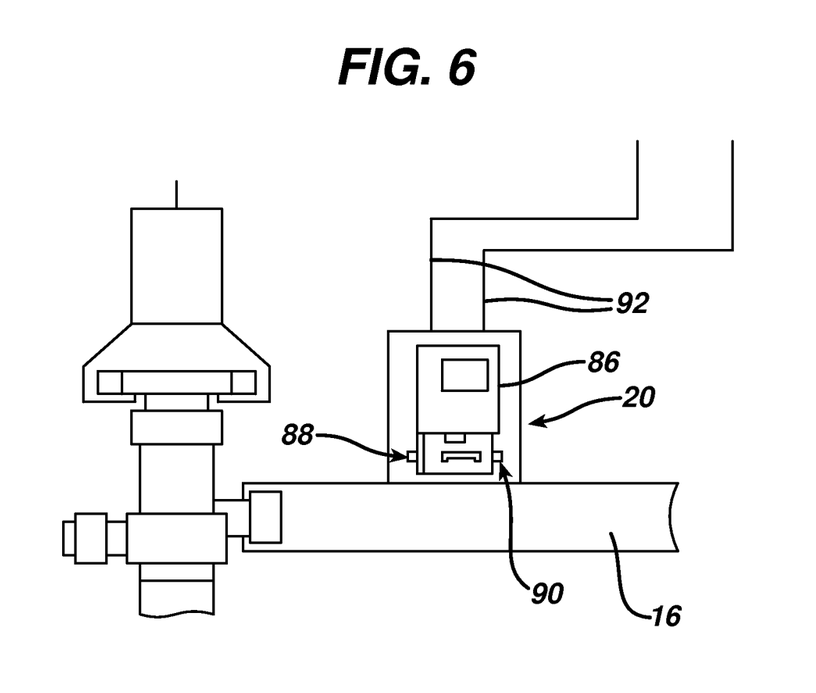
FIG. 6 is a schematic view of a portion of the monitoring function of the present invention.

Referring to FIG. 6, a portion of the monitoring means 20 is depicted. It includes a programmable gas mass flow meter and totalizer 86. Although not exactly portrayed, the flow meter is positioned in series in the tubing 16 via input and output ports 88 and 90. The flow meter 86 is connected via a cable 92. When the second set of voice commands is initiated, the monitoring function is initiated. As noted above, these commands would include at least START, VOLUME, and STOP. As noted above the voice commands are received by the control device 22 via the headset and produce a corresponding second set of electrical signals. The use of the voice command VOLUME here represents the user's inquiry as to the status of the quantity of fluid remaining in the canister 12.

The control device 22 produces a corresponding second set of electrical signals based on the voice commands for the monitoring mode. These signals assuming a wireless connection between a Smartphone and transceiver 56, are received at antenna 55 and processed by the transceiver signal circuit 56. The signals are conveyed to the relay board via circuit path 61. They are directed by a relay on the board 58 to an output conductor 96, and to the programmable flow meter 86 through cable 92. The programmable flow meter 86 is adaptable to allow for the electrical interrogation of many characteristics including the volume remaining of the fluid or oxygen that it is monitoring.

While the programmable flow meter can provide highly accurate readings of the various parameters that it measures, for purposes of this application, the flow meter 86 may be programmed to produce electrical signals corresponding to a coarse indication of the characteristic measured—in this case, the volume. So, for example, these relatively coarse indications could be "low", "medium" and "high". In the case of reporting on the volume of the canister, one of these coarse signals, for example, "medium", is generated and supplied through the relay card board 58. The relay that is activated for this monitoring mode receives the signal that is unique to the determination of the volume status of "medium" and routes it along circuit path 98 to the input of the digital to analog converter portion of the transceiver 56 for subsequent processing and transmittal back to the voice controlled device 22 via antenna 55.

As noted above, the voice controlled device contains a further software program or a modification of the first voice recognition software to generate a respective sensory signal corresponding to the received, respective third set of electrical signals. The voice controlled device 22 transmits that signal to the sensory member (in the preferred embodiment, the ear) via the fourth interconnect means 30. As noted above this would be in a standard Bluetooth® connection.

The flow meter 86 can be similarly programmed to produce a coarse response to a voice command directed to determining how much time remains for a particular canister at a given flow rate of oxygen. Following the format above, if instead of the use of the voice command VOLUME, for example, the command TIME were employed, this would be processed similar to the previous command. Here though, the command TIME could be introduced while the system is providing oxygen to the user. The programmable flow meter 86 would be adapted to provide a respective electrical signal coarsely indicating the time remaining which would be processed as above. The sensory signal could reply with the word "THIRTY", for example. The user would know that this would indicate thirty minutes remaining for the particular flow rate then operating.

A flow meter that is programmable as suggested above is available from the "Omega Engineering Company", in Stanford, Conn. A particular model number would be selected from their FMA-4100/4300 series. Technical information about the flow meter is available at Omega's web site.

Figure 7:
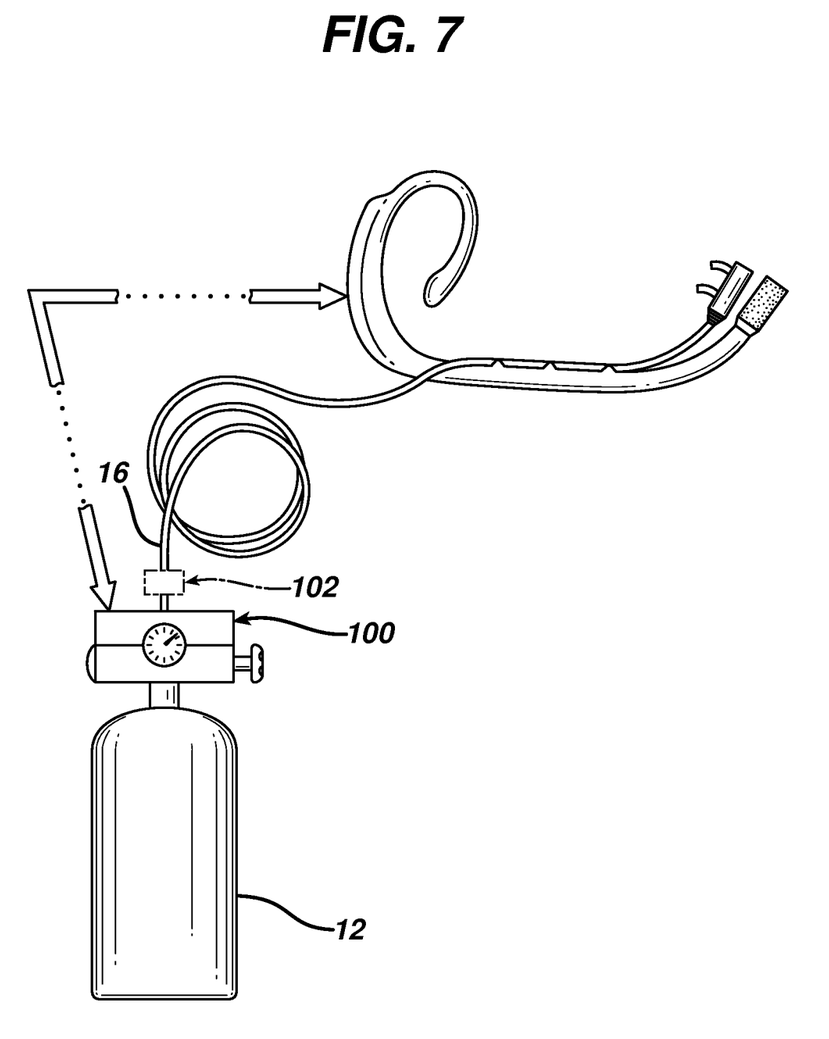
FIG. 7 is an alternate embodiment of the invention.

Referring to FIG. 7, a different embodiment employing the principles of the invention is depicted in simplified form. Here the canister 12 containing the fluid, such as the gas oxygen, is connected to a module 100. This module in effect includes essentially all the elements of FIG. 3 except for the voice controlled device or Smartphone, 22. So, the circuit board 52 including a transceiver module 56 are elements of the module 100. The electro-mechanical and mechanical elements of the system of FIG. 3 are also represented by the module 100. The electronic circuit board would include the voice recognition circuit 53. Suitable programming such as identified by that available from "Nuance Communications Inc." would be employed. Any speech to text requirement, particularly if the monitoring function is utilized, again can be found at the "Altera.com" web site at the address indicated above.

Shown in phantom in FIG. 7 is the means for monitoring function 102. This includes the flow meter 86 and a speech to text system again as outlined at the "Altera.com" web site at the specific address noted.

Figure 8:
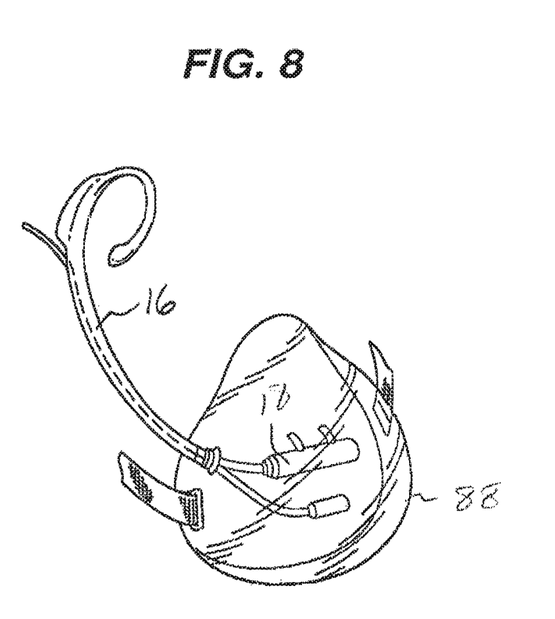
FIG. 8 is a perspective view of one embodiment of a facial mask which can be used to implement a part of the invention.
Figure 9:
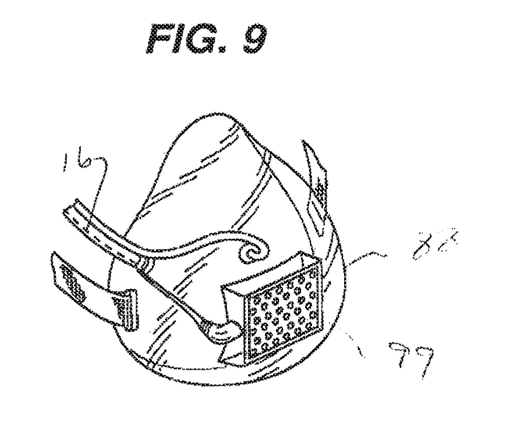
FIG. 9 is a perspective view of the facial mask of FIG. 8 which has been adapted to include a shutter member, whose open/close position can be controlled by an electrical signal.
Figure 10:
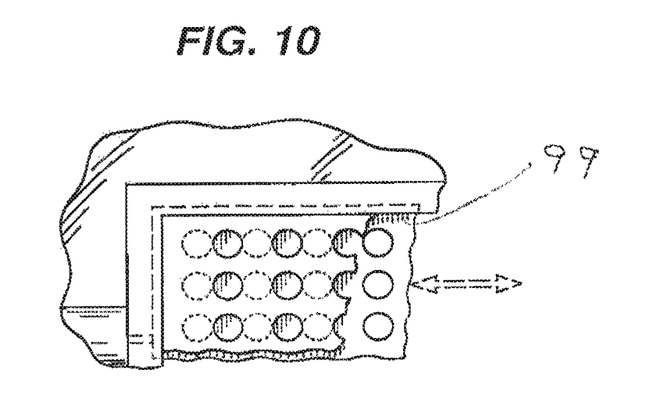
FIG. 10 is a partial, elevation view of the facial mask of FIG. 9 which depicts lateral movement of a shutter piece that can open or close-off air flow through the shutter member.

Referring to FIG. 8, the system incorporates a translucent mask 88 covering the nose and mouth region of the face, thereby providing protection from the elements and greater comfort. Such a mask incorporates a shutter type mechanism 99 (see FIGS. 9 and 10) that would be positioned in an orifice in front of the user's mouth. When oxygen is demanded, the user would vocalize the particular voice command required. An appropriate electrical signal would be generated by circuitry noted above, in response to the voice command START. The shutter 99 would be activated to a closed position. This would close the orifice when the required oxygen is delivered to the mask, so as to optimize the oxygen delivery. After a set period of time, or upon a further voice command, the shutter 99 would reopen. This would allow the user to breathe normally and converse when the oxygen delivery system is not being actively used.

Note that when the Smartphone's oxygen delivery VUI interface is not being actively used, the user would have full use of the Smartphone's other application (e.g., telephone, music system, etc.).

It is important to reiterate that the invention(s) described above does not in any way relate to the nature of the drug or chemical to be administered or the mechanism of such administration. This patent application only relates to the voice-activated control of the delivery, and the voice-activated monitoring of the status of any such device (whether on a wired basis or via a VUI and Bluetooth® enabled Smartphone). More importantly, the mechanisms described are intended to broadly apply to the hands-free and eyes-free voice activated control and monitoring of any device under any circumstances where such voice-activation would be beneficial, convenient and productive. Therefore, the particular discussion contained above relating to the voice activated delivery of oxygen is intended to be only illustrative of the general manner in which any device can be controlled and monitored via VUI voice activation using an appropriately equipped and programmed Smartphone.

When viewed from this perspective, the potential applications of this invention to increase the efficiency of almost any device or process by substituting voice-activated control and monitoring of such device or process without requiring the intervention of the user's hands and eyes, appears to be very broad indeed.

However, to the applicant's knowledge, certainly, no Smartphone or other VUI applications have yet been utilized for the actual control and monitoring of a device in the manner discussed herein.

While the disclosure above seems to imply that the user is one and the same as the person that benefits from the release of the fluid or oxygen, it is to be understood that the user can produce the results intended by the system for the benefit of another person, for example, a patient in a bed who is otherwise unable to speak or else provide for his or herself.

Also, although from the preferred embodiment it is apparent that a gas such as oxygen is provided to a person, other fluids, for example, those that might be carrying medicine, can be brought to a body part of the person receiving same such as through an intravenous needle disposed in a limb of the person benefited all as directed by another party, "the user".

The reader recognizes that the description set forth above is directed to applicant's preferred embodiment. The language employed must be viewed, not in a limiting way, but in a more encompassing manner The only limitation on the breadth of the invention must be as defined by the scope of the claims that follow.

What is claimed is:

1. Hands-free and eyes-free voice-activated wireless apparatus for administering oxygen to a user, comprising:
   a human-portable oxygen tank having a bluetooth-standard wireless electronic valve configured to release oxygen from the oxygen tank, the electronic valve having at least LOW and HIGH settings;
   a flexible tube supplying the released oxygen from the oxygen tank to a face of a user;
   a bluetooth-standard wireless microphone receiving voice commands from the user, the voice commands including at least START, STOP, LOW, HIGH, and VOLUME;
   a bluetooth-standard wireless earphone providing audible signals to the user which correspond to a quantity of oxygen remaining in the oxygen tank;
   a bluetooth-standard monitor monitoring an amount of oxygen in the oxygen tank, and outputting a corresponding oxygen volume signal; and
   a smartphone bluetooth-standard wirelessly coupled to (i) the bluetooth-standard wireless microphone, (ii) the bluetooth-standard wireless earphone, (iii) the electronic valve, and (iv) the bluetooth-standard monitor, the smartphone having at least one app stored therein that is configured to:
   voice-recognize the START command received from the wireless microphone and, in response thereto, at least one of (i) provide a wireless signal to the electronic valve to release oxygen from the oxygen tank, and (ii) provide a wireless signal to the monitor to start monitoring an amount of oxygen in the oxygen tank;
   voice-recognize the STOP command received from the wireless microphone and, in response thereto, at least one of (i) provide a wireless signal to the electronic valve to stop releasing oxygen from the oxygen tank, and (ii) provide a wireless signal to the monitor to stop monitoring an amount of oxygen in the oxygen tank;
   voice-recognize the LOW command received from the wireless microphone and, in response thereto, provide a wireless signal to the electronic valve to release oxygen from the oxygen tank at a first, low flow;
   voice-recognize the HIGH command received from the wireless microphone and, in response thereto, provide a wireless signal to the electronic valve to release oxygen from the oxygen tank at a second flow higher than the low flow;
   voice-recognize the VOLUME command received from the wireless microphone and, in response thereto, provide a wireless monitor signal to the monitor to generate the oxygen volume signal corresponding to the volume of oxygen in the oxygen tank; and the at least one app of the smartphone being further configured to (i) receive from the monitor a wireless volume signal corresponding to the oxygen volume signal, (ii) generate an output signal corresponding to the received volume signal, and (iii) provide a wireless earphone signal to the wireless earphone corresponding to the generated output signal; and the wireless earphone receiving the provided wireless earphone signal from the smartphone and, in response thereto, generating at least one of said audible signals, wherein the human-portable oxygen tank has a MEDIUM setting, and wherein the at least one app of the smartphone is configured to voice-recognize the MEDIUM command received from the wireless microphone and, in response thereto, provide a wireless signal to the electronic valve to release oxygen from the oxygen tank at a third flow, between the first flow and the second flow.

2. The apparatus according to claim 1, wherein the at least one app of the smartphone is configured to immediately respond to the VOLUME command received from the wireless microphone and provide the wireless monitor signal to the monitor to generate the oxygen volume signal corresponding to the volume of oxygen remaining in the oxygen tank at a time the wireless monitor signal is sent to the monitor.

3. The apparatus according to claim 1, wherein the at least one app of the smartphone being further configured to provide to the user at least one of the audible signals comprising at least one word.

4. The apparatus according to claim 1, wherein the bluetooth-standard wireless microphone and the bluetooth-standard wireless earphone are disposed in a single headset.

5. The apparatus according to claim 1, wherein the output signal corresponding to the received oxygen volume signal comprises a time signal.

6. The apparatus according to claim 1, wherein the output signal corresponding to the received oxygen volume signal comprises a percentage signal.

7. The apparatus according to claim 1, wherein the flexible tube includes a nose piece.

8. The apparatus according to claim 1, further comprising a user pack configured to carry the oxygen tank, the electronic valve, and the monitor.

9. Hands-free and eyes-free voice-activated wireless system for administering oxygen to a user, comprising:
 a human-portable oxygen tank having a bluetooth-standard wireless electronic valve configured to release oxygen from the oxygen tank, the electronic valve having at least LOW and HIGH settings;
 a flexible tube supplying the released oxygen from the oxygen tank to a face of a user;
 a bluetooth-standard wireless microphone receiving voice commands from the user, the voice commands including at least START, STOP, LOW, HIGH, and VOLUME;
 a bluetooth-standard wireless earphone providing audible signals to the user which correspond to a quantity of oxygen remaining in the oxygen tank;
 a bluetooth-standard monitor monitoring an amount of oxygen in the oxygen tank, and outputting a corresponding oxygen volume signal;
 a smartphone bluetooth-standard wirelessly coupled to (i) the bluetooth-standard wireless microphone, (ii) the bluetooth-standard wireless earphone, (iii) the electronic valve, and (iv) the bluetooth-standard monitor, and the smartphone having at least one app stored therein that is configured to cause the smartphone to:
 voice-recognize the START command received from the wireless microphone and, in response thereto, at least one of (i) provide a wireless signal to the electronic valve to release oxygen from the oxygen tank, and (ii) provide a wireless signal to the monitor to start monitoring an amount of oxygen in the oxygen tank;
 voice-recognize the STOP command received from the wireless microphone and, in response thereto, at least one of (i) provide a wireless signal to the electronic valve to stop releasing oxygen from the oxygen tank, and (ii) provide a wireless signal to the monitor to stop monitoring an amount of oxygen in the oxygen tank;
 voice-recognize the LOW command received from the wireless microphone and, in response thereto, provide a wireless signal to the electronic valve to release oxygen from the oxygen tank at a first, low flow;
 voice-recognize the HIGH command received from the wireless microphone and, in response thereto, provide a wireless signal to the electronic valve to release oxygen from the oxygen tank at a second flow higher than the low flow;
 voice-recognize the VOLUME command received from the wireless microphone and, in response thereto, provide a wireless monitor signal to the monitor to generate the oxygen volume signal corresponding to the volume of oxygen in the oxygen tank; and
 the at least one app being further configured to cause the smartphone to (i) receive from the monitor a wireless volume signal corresponding to the oxygen volume signal, (ii) generate an output signal corresponding to the received volume signal, and (iii) provide a wireless earphone signal to the wireless earphone corresponding to the generated output signal; and the wireless earphone receiving the provided wireless earphone signal from the smartphone app and, in response thereto, generating at least one of said audible signals wherein the human-portable oxygen tank has a MEDIUM setting, and wherein the at least one app is configured to cause the smartphone to voice-recognize the MEDIUM command received from the wireless microphone and, in response thereto, provide a wireless signal to the electronic valve to release oxygen from the oxygen tank at a third flow, between the first flow and the second flow.

10. The system according to claim 9, wherein the at least one app is further configured to cause the smartphone to display a visual monitored oxygen signal corresponding to the received volume signal.

11. The system according to claim 9, wherein the bluetooth-standard wireless microphone and the bluetooth-standard wireless earphone are disposed in a single headset.

12. The system according to claim 9, wherein the output signal corresponding to the received oxygen volume signal comprises a time signal.

13. The system according to claim 9, wherein the output signal corresponding to the received oxygen volume signal comprises a percentage signal.

14. The system according to claim 9, wherein the flexible tube includes a nose piece.

15. Hands-free and eyes-free voice-activated wireless method for administering oxygen to a user, comprising:
 providing a human-portable oxygen tank having a bluetooth-standard wireless electronic valve configured to release oxygen from the oxygen tank, the electronic valve having at least LOW and HIGH settings;

providing a flexible tube supplying the released oxygen from the oxygen tank to a face of a user;

providing a bluetooth-standard wireless microphone receiving voice commands from the user, the voice commands including at least START, STOP, LOW, HIGH, and VOLUME;

providing a bluetooth-standard wireless earphone providing audible signals to the user which correspond to a quantity of oxygen remaining in the oxygen tank;

providing a bluetooth-standard monitor monitoring an amount of oxygen in the oxygen tank, and outputting a corresponding oxygen volume signal; and providing a smartphone bluetooth-standard wirelessly coupled to (i) the bluetooth-standard wireless microphone, (ii) the bluetooth-standard wireless earphone, (iii) the electronic valve, and (iv) the bluetooth-standard monitor, the smartphone having at least one app stored therein that is configured to perform the steps of:

voice-recognizing the START command received from the wireless microphone and, in response thereto, at least one of (i) provide a wireless signal to the electronic valve to release oxygen from the oxygen tank, and (ii) provide a wireless signal to the monitor to start monitoring an amount of oxygen in the oxygen tank;

voice-recognizing the STOP command received from the wireless microphone and, in response thereto, at least one of (i) provide a wireless signal to the electronic valve to stop releasing oxygen from the oxygen tank, and (ii) provide a wireless signal to the monitor to stop monitoring an amount of oxygen in the oxygen tank;

voice-recognizing the LOW command received from the wireless microphone and, in response thereto, provide a wireless signal to the electronic valve to release oxygen from the oxygen tank at a first, low flow;

voice-recognizing the HIGH command received from the wireless microphone and, in response thereto, provide a wireless signal to the electronic valve to release oxygen from the oxygen tank at a second flow higher than the low flow;

voice-recognizing the VOLUME command received from the wireless microphone and, in response thereto, provide a wireless monitor signal to the monitor to generate the oxygen volume signal corresponding to the volume of oxygen in the oxygen tank; and the at least one app of the smartphone being further configured to perform the steps of (i) receiving from the monitor a wireless volume signal corresponding to the oxygen volume signal, (ii) generating an output signal corresponding to the received volume signal, and (iii) providing a wireless earphone signal to the wireless earphone corresponding to the generated output signal; and the wireless earphone receiving the provided wireless earphone signal from the smartphone and, in response thereto, generating at least one of said audible signals, wherein the human-portable oxygen tank has a MEDIUM setting, and wherein the at least one app of the smartphone is further configured to perform the step of voice-recognizing the MEDIUM command received from the wireless microphone and, in response thereto, provide a wireless signal to the electronic valve to release oxygen from the oxygen tank at a third flow, between the first flow and the second flow.

16. The method according to claim 15, wherein the at least one app is further configured to cause the smartphone to generate the output signal corresponding to the received volume signal, and to provide to the user at least one of the audible signals comprising at least one word.

17. The method according to claim 15, wherein the output signal corresponding to the received oxygen volume signal comprises a time signal.

18. The method according to claim 15, wherein the output signal corresponding to the received oxygen volume signal comprises a percentage signal.

* * * * *